United States Patent
Bonner et al.

(10) Patent No.: US 6,743,601 B1
(45) Date of Patent: *Jun. 1, 2004

(54) NON-CONTACT LASER CAPTURE MICRODISSECTION

(75) Inventors: Robert F. Bonner, Washington, DC (US); Seth R Goldstein, Bethesda, MD (US); Paul D. Smith, Annapolis, MD (US); Thomas Pohida, Monrovia, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/456,042

(22) Filed: Dec. 6, 1999

Related U.S. Application Data

(60) Provisional application No. 60/111,662, filed on Dec. 10, 1998.

(51) Int. Cl.$^7$ ................................................ G01N 1/30
(52) U.S. Cl. ................ 435/40.5; 435/6; 435/7.21; 435/7.23; 435/40.52; 436/177; 382/133; 428/346; 428/352
(58) Field of Search ............... 435/6, 7.21, 7.23, 435/40.5, 40.52, 4, 29, 7.29, 174, 156, 157, 100; 436/813, 174, 175, 177, 63; 428/346, 352; 382/133; 156/57

(56) References Cited

U.S. PATENT DOCUMENTS

| | | | |
|---|---|---|---|
| 4,012,475 A | 3/1977 | Kindel | 264/28 |
| 4,032,608 A | 6/1977 | Zinniger et al. | 264/46.6 |
| 4,545,831 A | 10/1985 | Ormstein | 156/57 |
| 4,624,915 A | 11/1986 | Schindler et al. | 435/4 |
| 4,629,687 A | 12/1986 | Schindler et al. | |
| 5,461,907 A | 10/1995 | Tech et al. | 73/105 |
| 5,843,657 A * | 12/1998 | Liotta et al. | 435/6 |
| 5,859,699 A | 1/1999 | Baer et al. | 356/246 |
| 5,866,417 A | 2/1999 | Matyas et al. | 435/378 |
| 5,985,085 A * | 11/1999 | Baer et al. | 156/285 |
| 6,010,888 A * | 1/2000 | Liotta et al. | 435/100 |
| 6,100,051 A * | 8/2000 | Goldstein et al. | 435/40.5 |
| 6,157,446 A | 12/2000 | Baer et al. | |
| 6,184,973 B1 | 2/2001 | Baer et al. | |
| 6,215,550 B1 | 4/2001 | Baer et al. | |
| 6,251,516 B1 * | 6/2001 | Bonner et al. | 428/346 |
| 6,420,132 B1 * | 7/2002 | Bonner et al. | 435/40.5 |

FOREIGN PATENT DOCUMENTS

| | | |
|---|---|---|
| EP | 0539888 A1 | 5/1993 |
| WO | WO 99 00658 A | 1/1999 |
| WO | WO 99 17094 A | 4/1999 |
| WO | WO 99 39176 A | 8/1999 |

* cited by examiner

Primary Examiner—Christopher Chin
Assistant Examiner—Gailene R. Gabel
(74) Attorney, Agent, or Firm—William Michael Hynes; Townsend and Townsend and Crew LLP

(57) ABSTRACT

An apparatus and process for the micro juxtaposition is set forth where a selectively activatable surface is maintained spaced apart from the tissue sample and juxtaposed to the tissue sample by activation. In the typical case, activation occurs by laser radiation with the material of the activatable surface thermally expanding and bringing about the desired micro juxtaposition. The disclosed micro juxtapositioning can cause locally and microscopically pressure on tissue sample, insertion to the tissue sample, or contact of an activated or prepared surface to the tissue sample.

15 Claims, 11 Drawing Sheets

NON-CONTACT LASER CAPTURE MICRODISSECTION

This application is a Continuation In Part and claims the benefit of U.S. Provisional Application 60/111,662 filed Dec. 10, 1998 entitled Non-Contact Laser Capture Microdissection, the disclosure of which is incorporated herein by reference.

This invention relates to a new method of laser capture microdissection. Generally, laser capture microdissection (here after also known as LCM) relates to a process of gathering samples of a specimen from a slide after visualization. In the process, an activatable surface is placed overlying the visualized specimen at a selected area, the surface activated to adhere to the specimen, and the activatable surface removed with the selected portion of the specimen attached.

In this disclosure of a new method of LCM, a physical process and designs for a thermally-activatable polymer layer are described in which the polymer on activation expands significantly in order to "reach out and grab" the target object within the microscopic field of interest. On cooling the activatable layer contracts (either during cooling or later in response to stored elastic stress) thereby bringing the "captured" microscopic target back closer to the original polymer surface. Using these physical processes and specific designs, "non-contact LCM" can be practiced by placing the selectively activatable coating at fixed separation distance (on the order of 5 to 20 microns) from the specimen, such as a tissue sample mounted on a slide. When a specimen has material selected from microdissection (typically by visualization within a microscope by transmission or epifluorescence) and the activatable coating activated with laser radiation, expansion and subsequent contraction of the activatable coating causes precise capture and extraction of the targeted elements within the sample. Activation may cause the surface to become adhesive (e.g., thermoplastic or photochemical bonding). In an alternative design, the specimen exposed side of the activatable coating can have a thin surface layer with the activatable coating forming a subsurface layer between a supporting substrate and the thin surface layer exposed to the specimen. The outward expansion of the subsurface layer brings the thin surface layer into contact with a complex tissue surface. In this alternative design, the surface layer can exhibit molecularly specific affinity for specific targets providing bonding specificity in addition to that of targeting the material selected for microdissection from the specimen.

BACKGROUND OF THE INVENTION

Microdissection of particular objects within a microscopic field have long been practiced in order to isolate specific elements from a complex field. This has been particularly important in complex biological samples where specific cells (e.g., stem cells) or clusters of cells (e.g., glomerulus from kidney) or even subcellular elements (such as a metaphase chromosome or a specific band of a chromosome) might be desired for subsequent biochemical analysis. Flow cytometry and cell sorting has been used for more than two decades to isolate specific populations of cells from single cell suspensions. In 1976, Meier-Ruge et al. described a pulsed UV-laser microscope, which was used to cut around the edges of invasive cancer cells in a tissue specimen in order to perform enzymatic activity analysis of such tissue. Schindler and Holland [patents] described a laser microscope used to isolate specific living cells from cell culture by either killing unwanted cells by a scanned laser beam or by cutting out all regions except those desired. Shibata et al. [Am. J Pathol. 141:539, 1992] described a similar process in which a simple UV-absorbing mask placed over specific microscopic regions of interest on a complex tissue section and the DNA in all other regions was damaged by UV irradiation. The small amounts on DNA in the protected regions could be extracted and amplified by polymerase chain reaction (PCR) in order to assess specific mutation in cancer cells within the tissue. Whetsell et al. [Oncogene 7:2355, 1992] described a variety of manual microdissection techniques applied to isolation and subsequent molecular analysis of pure populations of cells within the complex pathology specimen: including scraping target region with a needle or micropipette tip, injecting a fluid to make a cell suspension and then drawing the suspended microsample back into the tip for subsequent macromolecular analysis. In U.S. patent application Ser. No. 08/203,780 entitled Isolation of Cellular Material Under Microscopic Visualization by Lance A. Liotta, et al. filed Mar. 1, 1994, the idea of adhering visualized material on a specimen to a probe tip and then removing the tip with the procured sample to place in a solution for molecular analysis was described.

In U.S. patent application Ser. No. 08/544,388 entitled Isolation of Cellular Material Under Microscopic Visualization by Lance A. Liotta, et al. filed Oct. 10, 1995, the concept of microdissecting cancer cells in order to construct cDNA libraries of genes that are specifically expressed in those pure populations was disclosed. Two specific microdissection concepts were proposed: 1) manual "needle" microdissections and 2) focal activation by a light (laser) beam of an activatable bonding layer placed in contact with the tissue sample. The later concept has been developed into what is called laser capture microdissection [Emmert Buck et al. Science 274:998, 1996 and Bonner et al. Science 278:1481, 1997]. In that disclosure, microscopic visualization of a specimen occurred to select tissue for extraction. Thereafter, a film containing an activatable coating was placed on the specimen and activated by laser to a state where it adhered to the specimen at the selected material. When the activated film was removed, the adhered portion of the specimen was likewise removed effecting the desired dissection.

In this original LCM concept, the specificity of LCM is conferred by the focal bonding, which only occurs when a targeted region of the activatable film is activated. All other portions of the coating placed on the tissue sample were assumed to be nonbonding. In practice, tissue pathology sections presented irregular surfaces on a microscopic layer, and the thermoplastic polymer used for focal laser bonding to the targeted tissue sites can pick up peaks on the tissue surface or whole regions not strongly bonded to the underlying microscope slide. This problem led to the development of activatable polymer films that could be selectively cut or punched out in those regions where targeted transfers had occurred, thereby reducing dramatically non specific contamination arising from the large regions of the "transfer film" not activated by the laser.

In prior art with thermoplastic polymers used to create thermally activated bonds between two surface [here, the film substrate and the tissue section], it is known that the bond strength is dependent on applied pressure, fluidity of the melted polymer and time of activation. Thus the necessity for a strong bond to the tissue [i.e., stronger than the tissue bond strength to the glass microscope slide] would seem to require strong contact pressure or long activation pulses. In U.S. Provisional Patent Application Serial No. 60/094,871, filed Jul. 30, 1998 entitled PRECISION LASER CAPTURE MICRODISSECTION USING SHORT PULSE LENGTH by Robert F. Bonner, et al. it was disclosed that short pulses are required for and allow making the smallest LCM microdissections (e.g., <10 microns in diameter).

It is inherent in the Liotta 1995 disclosure that either the film is first contacted with the specimen and then activated [as described in Emmert-Buck et al. and in Bonner et al.] or alternatively, the activated region of the film is initially a short distance away from the specimen (microscopic) and only comes into contact with the specimen when activation occurs. However, in the original Liotta 1995 disclosure, there is always some part of the film in contact with the specimen. It is important to note that there is no suggestion of a deliberate spacing of all of the activatable coating from the specimen to obtain greater precision in the desired microdissection. In either event, the selected portion of the specimen adheres to the film and is pulled away with the film.

In PCT Application PCT/US96/16517 entitled Isolation of Cellular Material Under Microscopic Visualization by Lance A. Liotta, et al. filed Oct. 9, 1996; augmentation of the laser capture microdissection was set forth. The various films and activating energy sources were set forth.

U.S. patent application Ser. No. 09/364,927, filed Feb. 7, 1997, entitled ISOLATION OF CELLULAR MATERIAL UNDER MICROSCOPIC VISUALIZATION by Lance A. Liotta, et al. filed Feb. 4, 1998, further parameters relating to the basic technique of laser capture microdissection were set forth. Again, the specific advantages of deliberately maintaining a separation between the activatable coating and specimen were not specifically set forth.

In Provisional Patent Application Serial No. 60/073,480 filed Feb. 3, 1998 entitled MECHANICAL HANDLING SYSTEMS FOR LASER CAPTURE MICRODISSECTION by Seth R. Goldstein, Robert F. Bonner, et al the idea of having a deliberate spatial separation between the activatable coating and the specimen subject to laser capture microdissection was set forth.

U.S. Patent Application Ser. No. 08/883,821 entitled CONVEX GEOMETRY ADHESIVE FILM SYSTEM FOR LASER CAPTURE MICRODISSECTION by Seth R. Goldstein, Robert F. Bonner, et al., the use of a cylindrical surface was disclosed for holding a film useful for laser capture microdissection. In this application, a rod typically having a conical end—was contacted to a specimen. Thereafter, conventional activation occurred, typically by a laser activating a coating on the rod to adhere to a selected part of the specimen.

In U.S. Provisional Patent Application 60/073,480 filed Feb. 2, 1998 entitled Mechanical Handling Systems for Laser Capture Microdissection, by, Seth R. Goldstein and Robert F. Bonner we specifically set forth the advantage of having a small spatial separation between the layer which is activated and the specimen surface. This disclosure is hereby cross-referenced in this application as if set forth herein in full part.

Acting on this we now disclose the physics of utilizing the expansion of the transfer film volume focally activated by the laser pulse 1) to simultaneously span a small separation between the transfer surface and the tissue and 2) to create a contact force sufficient to cause the transfer surface to come into molecular contact necessary for forming a strong bond even in very brief pulses (e.g., <<1 msec). The use of this physical process leads to a variety of disclosed inventions utilizing both unique designs and properties of the activatable layer as well as supporting substrates and special surface coatings which are specifically designed to maintain this separation from the sample during Laser Capture Microdissection (LCM).

SUMMARY OF THE INVENTION

An LCM apparatus and process for the micro juxtaposition is set forth where a selectively activatable surface is maintained spaced apart from the tissue sample and juxtaposed to the tissue sample by activation. In the typical case, absorption of the laser radiation by the activatable thermoplastic layer causes a volumetric expansion confined to the direction of the target and brings about the desired micro juxtaposition. The disclosed micro-expansion of the activated volume can cause local contact with the targeted element within the complex sample and develop sufficient contact pressure to either 1) flow into all void spaces within the target (e.g., displacing air or fluid within it) and form a strong mechanical bond, or, 2) bring an activated or prepared surface into intimate molecular contact with the target sample in order to create a focal targeted and affinity specific bond (e.g., a cell with specific cell surface receptors which are brought in contact with specific high affinity ligands bonded to the prepared surface of the transfer film.

The selectively activatable layer (e.g., that layer specifically absorbing the laser pulse and bonding to the target at its bottom surface) usually has a non-absorbing supporting substrate adherent over the entire top surface. The bottom surface of the activatable layer is maintained at a distance typically between 5 to 20 microns from the specimen. This separation must be great enough to reproducibly insure that no part of the activatable transfer surface touches peaks of the specimen surface (e.g., peaks of the tissue surface irregularities) and therefore is dependent on the flatness or the uniformity of the specimen thickness.

In the preferred embodiments, non-contact LCM allows concentration of a series of targeted elements onto precise locations (e.g., placing 10 urn transfers onto a specific 20 um array of locations on the transfer film surface regardless of the original (larger) separation of these elements within the sample. This requires that the process of targeting, bonding and separation of individual elements within the sample can be repeated any number of times without altering the chosen separation distance. In this case, either the captured material must be brought back to flush with the original bottom surface of the activatable layer or close enough to it that the captured material is entirely above the top surface of the remaining sample.

In currently practiced forms of LCM, we have specifically chosen thermoplastic polymers which have a low melting temperature and a rapid decrease in viscosity with increasing temperature above the melting point, so as to be able to flow into the voids of tissue and form strong bonds rapidly at relatively low temperatures (~100 C). In order to achieve non-contact LCM in its most robust form, we further require a reversible large volume increase in the thermoplastic polymer as it melts, which can be recovered, as it resolidifies on cooling. In this manner the polymer when focally melted is forced to move a substantial fraction of its total thickness towards the target element in the microscopic specimen, spanning the separating gap and still expanding in order to fill the "fluid voids" within the sample or to surround the target element. Thus the thickness spanned is approximately equal to the gap separation plus the sample specimen thickness. Usually the LCM thermoplastic polymers cool so rapidly after the end of the laser pulse (due to the high thermal conductivity of the microscope slide on which the specimen is mounted), that the polymer within the activated volume freezes in a stretched state (i.e., is focally elastically deformed).

By using strong, long chain thermoplastic polymers with a large phase transition on melting (such as Dupont ELVAX 410 or 4310), the activated polymer can move large distances (>20 microns for a 100 um thick layer) where melted, rapidly form a strong bond with the target, and retain hold of the targeted element as it is separated from its bond with the microscope slide (and its original untargeted sample elements) and then elastically retract releasing the elastic stress. Using this large movement and subsequent elastic contraction, a 10 um thick target element separated 10 um from the original transfer surface can be "found" (gap spanned), its voids filled and strongly bonded by the activated polymer, and then pulled back more than 10 um towards the transfer film substrate so that it is above the peaks of the untransferred specimen (e.g., tissue section surface irregularities.

The activated polymer can reach even greater distances than that predicted by its change in thickness or its fractional volume change on melting and heating times its original thickness (typically ~20% of film thickness). This can be accomplished by heating without melting the surrounding polymer, which expands into the melted core cylinder. This expansion into the melted core cylinder effectively squeezes the central core to move farther. Similarly the dynamics of the rapid melting and expansion and then cooling and a radial temperature gradient, permit the center of the activated polymer to inch towards the target specimen in a series of pulses (forming a central peak and a surrounding annular depletion zone). Additionally applying greater powers to the top surface of the thermoplastic polymer can cause the polymer at the top surface to vaporize into a vapor bubble at the same time the bottom surface melts. The pressure of the vapor bubble propels the activated polymer even farther distances [that is the volume change on vaporization is much larger than that of melting]. Generally the rapid cooling of the polymer freezes the expanded bubble. If after capture and separation of the target due to this large expansion, a second lower energy pulse re-melts the polymer and allows the air bubble (a partial vacuum) to collapse, large elastic recoils achieved.

Alternatively, air bubbles or low-temperature-vaporizable fluid volumes can be placed in the upper regions of the polymer film to augment its ability to span large gaps between the target specimen and the unactivated polymer surface. In all such refinements, greater reversibility of the expansion is preferred, since this more completely brings the LCM captured element back flush with the original polymer surface. For example, if the expansion of the activated polymer layer is fully reversible and the 10 um-thick, targeted element has a void fraction of 70% which is completely filled by the expanding polymer, then we would expect the captured tissue element to stick out only 3 um from the unactivated polymer surface. Thus if the surface peaks of the tissue are +3 um and the original gap is more than 5 um, the captured samples will be brought back sufficiently so that when the film and its substrate are replaced at the original average separation of the transfer surface with the tissue surface contact will not occur. Adjacent unactivated polymer surface can be used to target additional elements without any fear that the previous captured elements will touch the surface of the sample. Such a procedure allows multiple elements to be transferred in a series of steps to any proscribed array of side-by-side "parking places" on the transfer film. This concentration feature is very important whenever the subsequent analysis (either molecular or optical) requires improved sensitivity and specificity, faster reaction rate, and lower costs associated with smaller volumes of reagents.

The required spatial separation or gap can be maintained by the structure of supporting substrate and selectively activatable surface, the structure of the holder for the selectively activatable surface, the structure of a holder which makes contact with the tissue sample or reference surface, or even mechanisms for maintaining designed spatial separation such as air bearings or cantilevering methods. Methods are disclosed for establishing the desired spatial separation.

When the selectively activatable surface is activated, it expands into contact with the tissue sample to juxtapose to the specimen. This selectively activatable surface can then be adhesive with respect to the tissue sample, exert pressure on the tissue sample, manipulate the tissue sample, or bring a prepared surface into local microscopically controlled contact with the tissue sample.

Thus, this disclosure describes a method not known in the prior art, of creating focally specific juxtaposition between two surfaces normally not in contact, but brought into contact by focal activation of a film layer. This focally specific activation causes the movement of one surface towards the other so that intimate contact is made only at the activated sites on the surface.

In the usual case, the establishment of a local bond is desired when the two surfaces are brought together. This local bond can be of a number of different forms:

1) Thermoplastic injection of polymer into voids of the target sample and rapid solidification into a strong focal mechanical bond,
2) Thermoplastic expansion of a polymer to bind to specific tethers (e.g., polystyrene latex microspheres antibody linked to specific cells in the sample) by mechanical or high surface affinity as the expanding surface engulfs the tether (sphere),
3) Thermoplastic expansion of a polymer surface to make intimate molecular contact of a monolayer coating on the polymer surface with the cell surface—so that specific ligands on the outer surface of the monolayer can make high affinity, strong specific bonds to the cell surface of interest (e.g., cells that have specific receptor for the ligands) [this adds specific selection based on the unseen molecular composition of the target to previous microscopic targeting decisions],
4) Thermoplastic expansion of the polymer between cells to bond to an underlying polymer film of high strength and affinity for the thermoplastic polymer (e.g., forming a basket around the cells of interest—particularly useful for whole living cells or the smallest microscopically observable objects such as individual chromosomes or organelles), and
5) Thermoplastic injection of a polymer into the voids of a desiccated tissue section so that high affinity surfaces of the polymer bind to specific macromolecules within the target cells [this allows the polymer to act as an affinity column to provide means of purification of specific molecular components from targeted specimens).

Intrinsic to enablement of these methods is the discovery that focal activation of a thermoplastic polymer film and its volumetric expansion with focal heating causes the polymer surface to focally expand in reliable dose dependent distances. The thermoplastic polymer can then expand to span a separation with the target sample, bringing these two surfaces into focal contact. This expansion can be caused by:

1) A linear thermal expansion coefficient with heating and inertial confinement of the focally heated polymer on all sides except the surface facing the sample tissue (or target), 2) A volume increase in the polymer as it undergoes a phase transition from solid (e.g., crystalline) to liquid with heating and inertial confinement of the focally heated polymer on all sides except the surface facing the target, and 3) A rapid pressure transient caused by heating an air bubble enclosed within the targeted thermoplastic polymer which becomes focally fluid (i.e., lowered viscosity) and therefore focally responsive to this increased focal pressure.

We have discovered that low melting temperature EVA films (e.g., Elvax 410, 200W, and 4310 formulations) dyed with naphthalocyanines when focally melted by a near infrared laser diode pulse can be made to elastically expand tens of microns. This expanded material can make contact with a new surface originally separated by such distances, and then forms a strong bond with this new surface on rapid cooling which at the same time creates a stress in the elastic polymer. On breaking the attachment of the targeted sample with its substrate, the elastic stress in the polymer is released allowing the bonded target to be brought back towards the original polymer surface. Utilizing this mechanism it is possible to move the polymer surface out to find a surface of a target, to conform to this surface on a molecular level. During the pulse, a non-stressed molecular interaction of the two surfaces can be accomplished so those specific molecular bonds can be formed prior to the rapid cooling of the polymer (after the pulse is stopped). This allows the target to be physically bound to the polymer film and through it to the film's underlying solid substrate.

As distinct from previous LCM, these mechanisms allow:

1) The focal capture of targets without prior contact (thereby avoiding nonspecific interactions and partial transfer common to previous LCM methods), 2) Repetitive sampling of different regions of complex samples (with the same morphological and/or molecular surface identity) and bonding onto one or more precisely specified regions of the transfer film (e.g., multiple targets can be placed close together on a flat film regardless on the original spacing in the complex (tissue) sample(s)), thereby efficiently concentrating rare elements onto a small defined area of the transfer surface [permitting efficient microscopic examination and in situ labeling as well as efficient extraction of macromolecules from such pooled samples into extremely small volumes], 3) The possibility of further macromolecular specificity in the capture process by targeting cells by specific macromolecular targets as well as morphological identification by simultaneous microscopic imaging, and 4) Allowing the capture of wet samples surfaces and living cells by specific binding of mechanical linkers to the cell surface (previous LCM methods did not effectively bound in the presence of water).

In order to use the special properties of reproducible expansion and retraction of a thermoplastic polymer during focal heating and cooling, it is necessary to devise new methods of creating precise separations between the unactivated polymer and the target surface (e.g., 5–10 um thick section of a complex tissue). For example, we describe processes for making a polymer surface activated by a focused light beam (e.g., near IR laser diode) so that precise distances on the order of 5 to 20 microns separate this surface from the target sample. This can be done by a border material or precision spacer, which does not form a bond with a tissue, or biological preparation surface to which it is pressed.

Further this method includes a pressure plate which places the border zone in direct contact with the tissue surface while holding the activatable polymer surface at a fixed distance from the tissue surface (which is usually greater than the thickness of the tissue specimen but much less than the thickness of the polymer layer). Using previously disclosed LCM concepts and materials, this assembly can be placed onto a region of interest, the specific tissue components identified by the microscope and targeted by the laser beam. The laser beam when applied heats the polymer causing it to expand and make contact and bond (e.g., impregnate fluid or air spaces in the targets and then cool in place form a focally strong bond to the target).

We have shown that the standard EVA polymer we have been using for LCM (Dupont ELVAX 410 ethylene vinyl acetate) typically expands by >10% when focally heated from room temperature to its melting point. Thus if the targeted polymer film is melted from top to bottom at a focal spot, it will expand forward as a pedestal roughly 10% of film thickness. Thus a 100-micron thick film when focally melted will expand greater than 10 microns and thus can explore an air gap of this thickness between it and the tissue until it finds the tissue. When it finds the tissue, it expands into the void spaces of the tissue forming a strong focal bond.

We have observed that the actual distances traveled can be 2–3 fold greater than these values due to higher temperatures reached in the irradiated segment. This expansion is believed due to radial heat flow causing the surrounding solid polymer to radially constrict the melted zone pushing the polymer pedestal even farther from the original polymer surface. In general when the polymer cools it remains extended within the tissue until the film is rapidly "peeled" or lifted off the tissue (biological) specimen which tears at the borders of impregnated zone (typically a cylindrical pedestal). At this point the polymer and impregnated targeted tissue snaps back towards the original polymer surface. Typically the recoil is greater than 50% of the original extension. Thus with our existing EVA polymer used in LCM, we can activate a 100 micron thick polymer layer to extend 10 microns so as to cross a uniform 5 micron air gap, then impregnate a 5 micron thick tissue slice to which it bonds strongly. On separation from the tissue, the tissue polymer surface retract more than 5 microns so that this region may be placed again onto a different region of the tissue specimen without making contact anywhere except the border zone previously mentioned.

Thus repetitive transfer of different spots may be made (by appropriate translation of the film and its substrate) and concentrated (i.e., placed at target to target spacing that are much less than those within the tissue section) in a small central zone on the transfer surface. Once sufficient homogeneous biological targets have been accumulated on this transfer surface, it may be placed on or in a micro vessel for extraction and molecular analysis.

A specific refinement of this placement process includes the annular sealing of the thermoplastic film to the open top of a (cylindrical) micro chamber. This sealing occurs in a manner which seals the chamber with the transferred tissue (biological targets) placed at the center of the chamber or the inside surface of the polymer forming the lid. A further specific refinement uses the thermoplastic sealing properties of the EVA film to form this tight seal either by an annular laser source (or spot scanned in a circle) or by an annular heated pressure plate. This later approach is more easily realized if the substrate on which the recessed thermoplastic polymer was originally formed is relatively thin such as a 100–200 micron thick Mylar (polyester) film.

A specific preferred geometry is to manufacture a "non-stick" polymer tape so that its room temperature thickness is larger than that of the desired thermoplastic adhesive polymer thickness by the amount of the desired recess for the activatible polymer. This can be accomplished by manufacture of the EVA by casting onto the substrate at a higher temperature so that the differential expansion of the EVA and "nonstick" border cause the EVA to form a flat surface at the elevated temperature which on cooling leads to the desired recess. For example, we could form a laminate of 200 micron thick polyester (1 cm wide) with 200 micron thick strips of polyamide (3 um wide) on both edges) to form a central channel 4 mm thick. In the interval formed by this construction, a fine continuous bead (rod) of hot Elvax 410 (with IR absorbing dye) is extruded. The extruded material is then hot rolled by a smooth drum to form a flat surface. On cooling the extruded material leaves a 1 cm wide tape with a 4 mm wide central section of ELVAX 410 on polyester which is recessed by 20 microns from the border strips of polyimide bonded to the polyester. Thus we propose a simple scheme for the manufacture of a precision recessed tape for "non-contact LCM". Note that an alternative is to form the same sort of release surface (polyimide) border on a rigid substrate and then fill the central region with EVA.

A further refinement of non-contact LCM uses a previously disclosed design for periodic marking of the tape so that transfer could be placed periodically in well defined locations. Originally this concept was developed so that the punching out of small-transferred regions into extraction and molecular analysis vessels could be performed without a separate optical location of the transfer regions. In its present usage, a "non-contact LCM" tape can be translated a fixed increment relative to periodic indicator markers. Between each set of LCM transfers, sample can be gathered. At the end of the process, a set of multiple transfers of individual targets, which are homogeneous, can be pooled into one sample for molecular analysis. Much smaller separations between the individual LCM transfers within each set of transfers creates a cluster for each set within a small region (in the example above it might be within 0.5 mm while different sets might be spaced on 2 mm centers). The micro chambers used for molecular extraction and analysis can be formed as a linear array of wells (with a diameter slightly greater than the individual transfer clusters or d>0.5 mm in the above example) with exactly the same periodic repeat as tape translation between micro transfer sets (2 mm in the example above). This scheme allows a large number of sets of transfers to be accumulated onto the continuous tape and then continuously transferred and (heat) sealed onto the linear array of micro chambers for molecular extraction and analysis. This greatly increasing the efficiency of the current LCM process and provides means to reduce the volume of the molecular analysis systems to such small volume that the analysis may be performed more rapidly, at lower reagent cost, and with greater precision. Further this design or its analogues would offer significant advantages for automation of analysis and tracking of samples over the current LCM transfer caps, particularly when incorporating state of the art fluidic processing of micro volumes).

Furthermore, noncontact can be achieved by a tape and pressure plate by a variety of means that we are currently demonstrating in which there is no contact between the tape and the specimen except where activated. For example, the tape can be a uniform thickness which is the less than the gap between the pressure plate/rigid substrate and the target specimen surface by exactly the desired noncontact gap. By way of further example the top of the glass slide on which the specimen (e.g., 5 microns thick tissue slice) is placed is held against a defined stage surface near its edges where there is no specimen. In this latter case the pressure plate or rigid substrate for the LCM transfer film is mechanically positioned exactly 72 microns above the top of the glass slide, the tape is uniformly 60 microns thick and held against the lower surface of the pressure plate. The tissue section on the glass slide was made to be 5 microns thick (by adjusting the microtome which sectioned the tissue). In this case, the lower surface of the transfer film will be 7 microns above the tissue specimen nearest surface—only on activation with the transfer film contact the tissue specimen and only at the desired target spot. Note that if the pressure plate is spherical or ellipsoidal, then translation of the tape after laser activation and separation (standard LCM steps), the previously transferred region will be further removed from the tissue surface and the necessary "recoil" for flat film noncontact LCM with concentration is no longer necessary. This is the simplest film and means of performing non-contact LCM and if the separation means we are currently testing or alternative ones are easy to commercially precisely define and maintain; then this variant of non-contact LCM is likely to be the most widely used.

Although spacers attached to the transfer surface are potentially easy to manufacture and we discuss several ways to accomplish that, non-contact LCM is a fundamental method for capture and concentration. It relies on the expansion of the heated polymer sufficiently to span a gap and capture a target immediately below it (in the conventional sense of below). It offers many advantages such as concentration of rare objects, specific transfer and accumulation of a series of targets to specified locations on the transfer film that assists in subsequent analysis—(e.g., by placing into a microanalysis chamber with sub-microliter volumes). It is possible to design electromechanical/optical systems that allow precise placement of the transfer film at a specified gap above the desired target even if the bottom surface of the transfer film is flat or convex. We have built a couple of such systems and are evaluating their relative advantages over the film with intrinsic offset spacings on it.

Since the filing of the above referenced Provisional Patent Application Serial No. 60/111,662 filed Dec. 10, 1999 entitled Non-Contact Laser Capture Microdissection, we have made an important discovery which is detailed with respect to FIGS. 1G and 1H included herewith. Specifically, we have found that after a selected portion of a specimen is microdissected, it is possible to substantially collapse and substantially eliminate any pedestal of material on the activatable material. This can be accomplished by using a second pulse of exciting radiation after the microdissection capture and separation has been completed. This retraction of the pedestal has been found to be repeatable and predictable. It has the advantage of preventing inadvertent loss or contamination of the collected selected portions of material from the specimen and enables concentration of like cells to adjacent portions of the collecting substrate.

BRIEF DESCRIPTION OF THE DRAWINGS

FIGS. 1A–1F are respective views of the activatable coating under activation by a laser with:

FIG. 1A illustrating the initial activation overlying a sample;

FIG. 1B illustrating the full activation and contact of the activated lower portion with the material of the sample;

FIG. 1C illustrates the polymer contracting under stress;

FIG. 1D illustrates the targeted portion of the tissue sample attached to the now cooled activatable material;

FIG. 1E illustrates relative movement of the activatable coating relative to the sample to enable concentration;

FIG. 1F illustrates the extrusion of a pedestal for collecting a targeted specimen;

FIG. 2A illustrates the non-sticky border placed at spaced apart locations on a tape like substrate for receiving the activatable coating;

FIG. 2B illustrates the placement of molten coating on the substrate between the non-sticky borders;

FIG. 2C illustrates the substrate of FIG. 2B placed against an optical flat for cooling;

FIG. 2D illustrates the substrate of FIG. 2C after the coating on the substrate has cooled, it being noted that a small separation now exists from the bottom of the coating to the optical flat;

FIG. 2E illustrates the substrate of FIG. 2D now juxtaposed overlying a specimen with contact to the specimen occurring only at the non sticky borders and illustrating the activatable coating recessed from the specimen;

FIG. 2F illustrates the substrate and specimen of FIG. 2E illustrating the activation of the activatable coating by a laser such as illustrated in FIG. 1 and more particularly showing the swelling of the activatable coating to form a column for contact with a selected area of the specimen;

FIG. 2G illustrates the substrate of FIG. 2F removed from the specimen, the column shrunk and retracted with the selected portion of the specimen attached; and, FIG. 2H illustrates the substrate placed to a different specimen with like tissue being selected from that specimen to a site immediately adjacent the collection site of FIG. 2F;

FIGS. 7A–7C are embodiments of activatable surface holders that effect spatial separation of activatable surfaces from tissue sample wherein:

FIG. 7A illustrates a vacuum actuated holder for resting on a reference surface relative to the tissue sample and holding the activatable surface a spaced distance apart from the tissue sample;

FIG. 7B illustrates a vacuum holder similar to FIG. 7A with the inside surface of the holder being rounded;

FIG. 7C illustrates a vacuum holder similar to FIG. 7B with the activatable surface occupying all of the material within the holder excepting for non-adhesive coatings in contact with the slide surfaces;

FIG. 8A illustrates the activatable surface being confined within the holder and establishing its separation from the tissue sample from the holder;

FIG. 8B illustrates a holder with an actuator for effecting separation of the selected material from the tissue sample;

FIGS. 10A–10C are embodiments where there is no contact with either the tape or the tape holder with the tissue sample with:

FIG. 10A illustrating the case where the tape holder is cantilevered relative to the tape holder;

FIG. 10B illustrating the case where the tape is pivoted on simple beam relative to the tissue sample with viewing of the sample occurring along a so-called EPI path through the slide into the sample;

FIG. 10C is a side elevation of a convex surface apparatus utilizing this invention;

DESCRIPTION OF THE SPECIFIC EMBODIMENTS

Figure 1:
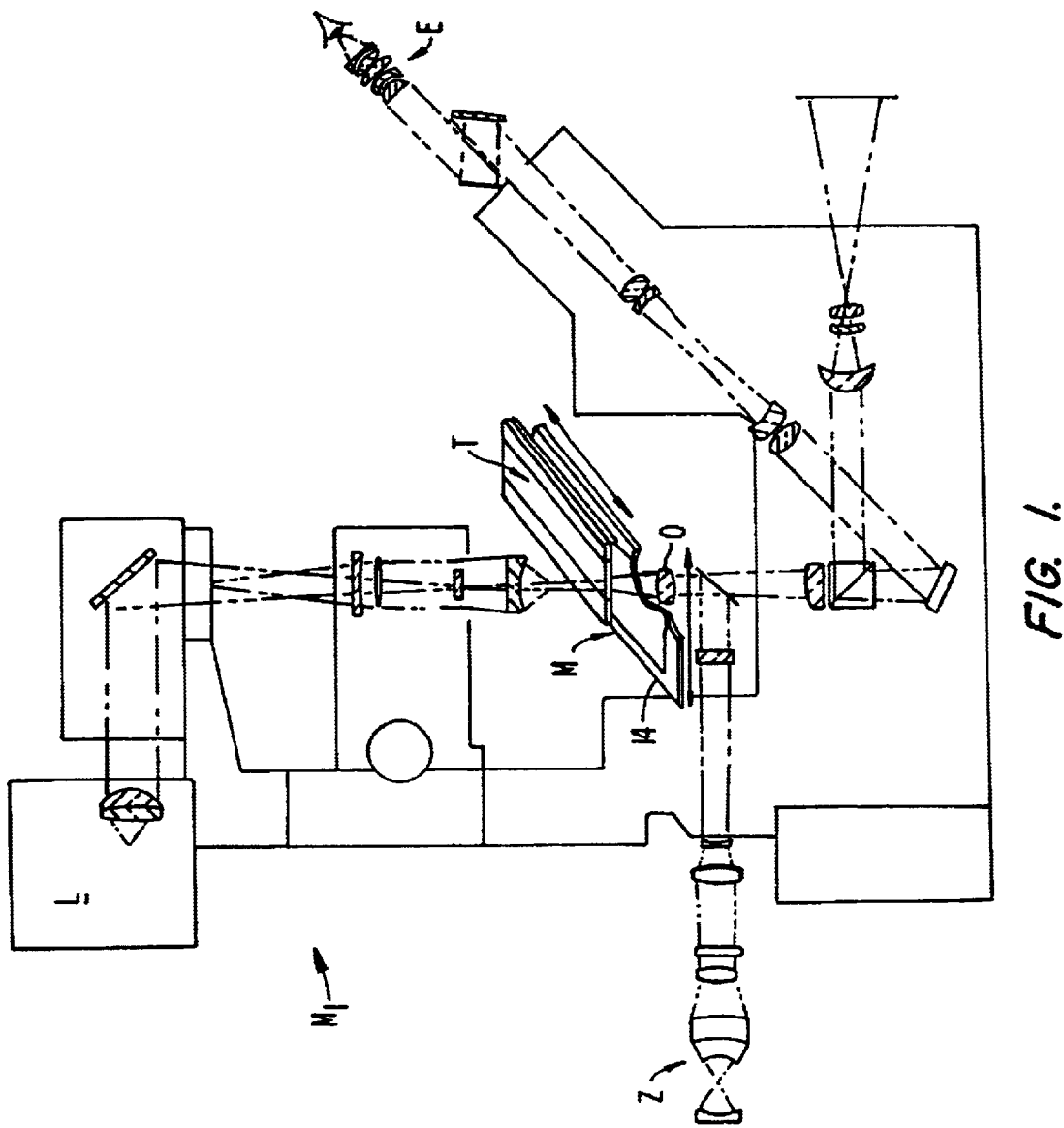
FIG. 1 is a perspective view of laser capture microdissection illustrating a microscope effecting visualization of a specimen, an activatable coating on a substrate overlying the specimen, and a laser for activating the activatable coating.

Referring to FIG. 1, laser capture microdissection is schematically illustrated with respect to a so-called EPI microscope having a view path that comes from the bottom of specimen M mounted on slide 14. Light source L illuminates specimen M. At the same time, eyepiece E views the specimen along an inverted path from underneath specimen M. Specifically, the specimen M is visualized at a selected portion M1. When this portion is selected, laser capture microdissection as further described in this disclosure occurs. As a part of this dissection, it is required that a laser source Z be incident upon an activatable coating contained on tape T.

Thus, this disclosure describes a method not known in the prior art, of making a polymer surface activated by a focused light beam (e.g., near IR laser diode) so that this surface is recessed by precise distances on the order of 5 to 20 microns or more from a border material. This boarder material does not form a bond with tissue or biological preparation surface to which it is pressed (See FIG. 2D). Further this method includes a pressure plate (e.g., cylindrical rod R—see FIG. 6) which places the border zone or rim 16 in direct contact with the tissue surface while holding the activatible polymer surface 18 at a fixed distance from the tissue surface (which is usually greater than the thickness of the tissue specimen but much less than the thickness of the polymer layer). Using previously disclosed LCM concepts and materials, this assembly can be placed onto a region of interest, specific tissue components identified by the microscope and targeted by the laser beam which heats the polymer causing it to expand and make contact and bond (e.g., impregnate fluid or air spaces in the targets and then cool in place form a focally strong bond to the target).

Figure 1A:
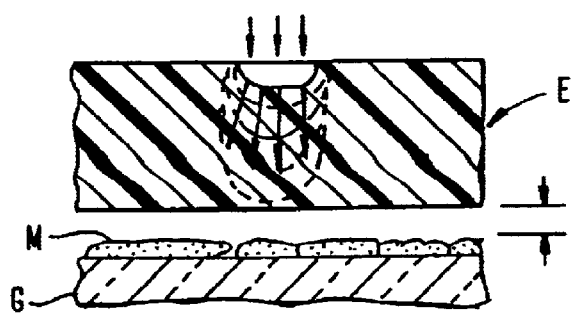

FIGS. 1A–1E all illustrating in a cartoon sequence the activation. In FIG. 1A, during the pulses from a laser the volume of activatable material E slowly increases. It will be noted that between sample M and the lower surface of the activatable material E that a consistent gap in the range of 5 to 20 microns exists.

Figure 1B:
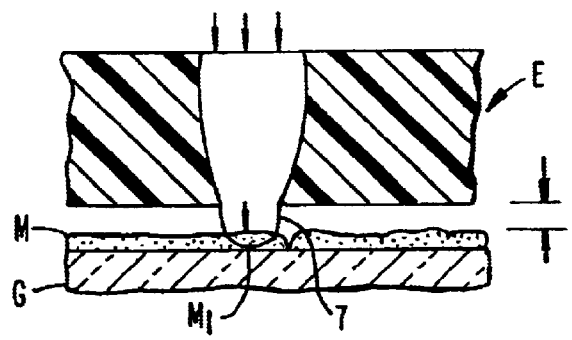

Referring to FIG. 1B, it will be seen that the full volume of activable material E is activated. This causes expansion of lower portion 7 for contact to and in this case bonding with selected portion $M_1$ of specimen M.

Figure 1C:
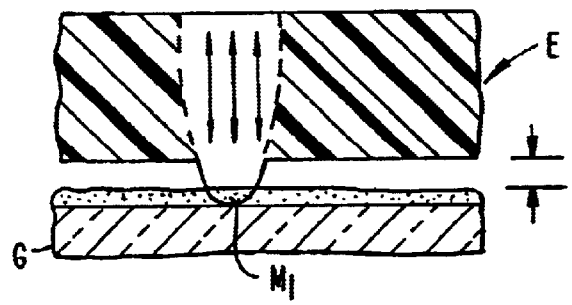
Figure 1D:
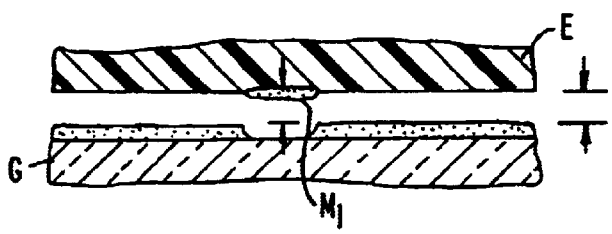

Referring to FIG. 1C, it will be seen that the expanded and activated material E has now cooled. This results in the elongated portion become elastically stressed or stretched. The reader will understand that in some cases, the stretching will in fact cause selected portion of sample $M_1$ to be completely separated as shown in FIG. 1D. Alternately, and referring to FIG. 1D, activatable layer E can be withdrawn a sufficient distance to cause the desired microdissection and relaxation of stress in activatable layer E. In either event, the configuration of FIG. 1D results.

Figure 1E:
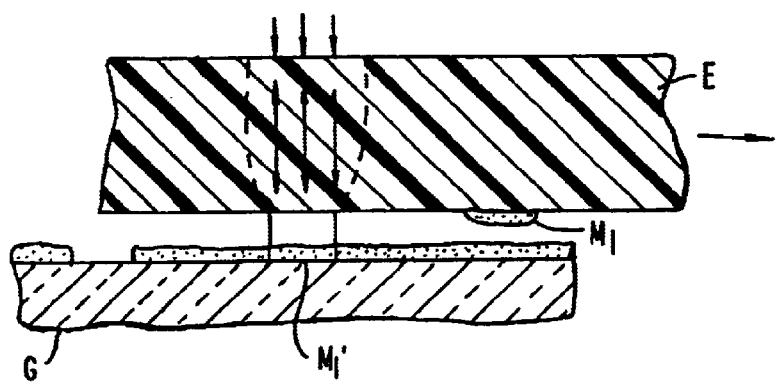

Referring to FIG. 1E, relative translation of the activatable material E relative to the sample occurs. In this case, what were originally separated selected portions of the sample can be concentrated.

Figure 1F:
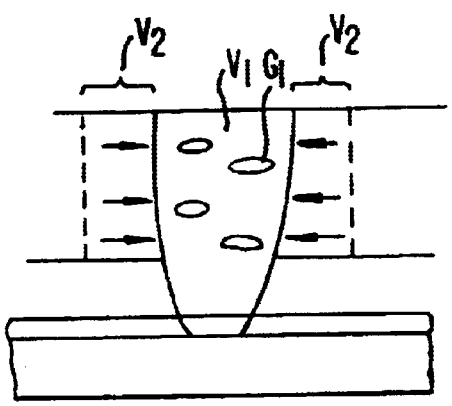

Finally, and referring to FIG. 1F, two additional phenomena are illustrated. First, activatable material E is shown with a first volume $V_1$ activated. In this volume gas bubbles G are illustrated which assist expansion. The gas bubbles can be gas previously placed or dissolved within the material, volatile components of the activatable material, or virtually any component which upon activation creates gas within the activated volume $V_1$.

Secondly, and again referring to FIG. 1F, it is possible to activate a generally cylindrical volume $V_2$ about inner volume $V_1$. This cylindrical volume $V_2$ has the general effect of creating expansion of the cylindrical volume with components toward volume $V_1$. This causes the activatable material E to expand away in a manner not unlike toothpaste being squeezed from a tube. Unlike this latter example, when the activatable material cools, contraction of the effectively extruded volume can occur.

Figure 2A:
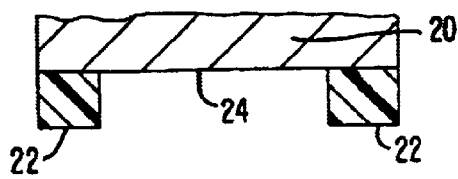
FIGS. 2A–H are a side elevation of a cartoon series where.
Figure 2B:
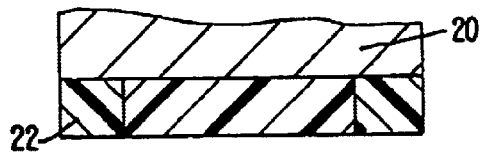
Figure 2C:
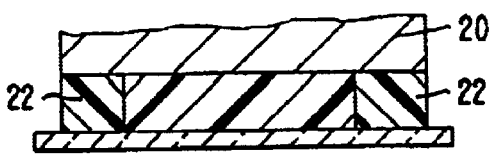
Figure 2D:
Figure 2E:
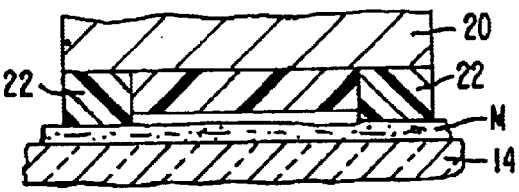
Figure 2F:
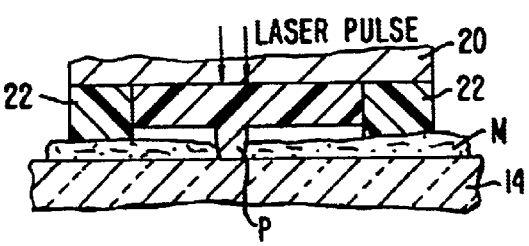
Figure 2G:
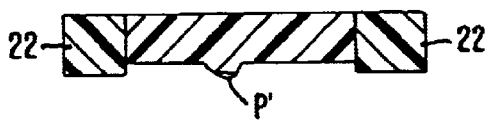

Referring to FIG. 2F, we have shown that the EVA polymers we have used for LCM (Dupont ELVAX 410 & 200W & 4310 ethylene vinyl acetates) typically expand by >10% when focally heated from room temperature to its melting point. Thus if the targeted polymer film is melted from top to bottom at a focal spot, it will expand forward as pedestal P greater than 10% of the film thickness. As shown in FIG. 2F, this occurs toward specimen M on slide 14. Thus a 100-micron thick film when focally melted will expand greater than 10 microns. The expanded polymer can thus explore an air gap of this thickness between it and the tissue until it finds the tissue. When the expanding column finds the tissue or pedestal P, the column at the point of contact expands into the void spaces of the tissue forming a strong focal bond.

We have observed and discovered that the actual distances traveled can be 2–3 fold greater than these values. This excess expansion is believed due in part to higher temperatures reached in the irradiated segment and due to radial heat flow causing the surrounding solid polymer to radially constrict the melted zone. This radial constriction of the melted zone pushes the polymer pedestal P even farther from the original polymer surface.

In general when the polymer cools it remains extended within the tissue until the film is rapidly "peeled" or lifted off the tissue of the (biological) specimen. This lifting of the pedestal tears at the borders of impregnated zone (typically a cylindrical pedestal). At this point the polymer and impregnated targeted tissue snaps back towards the original polymer surface as retracted pedestal P'.

Figure 1G:
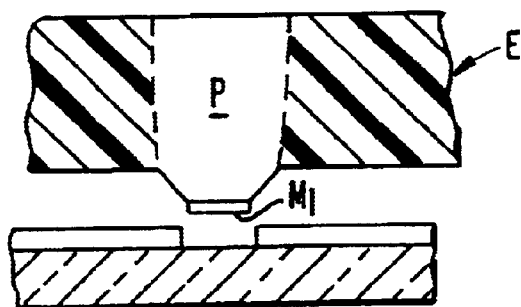
FIG. 1G illustrates a pedestal with specimen (here shown similar to the specimen and pedestal of FIG. 1F) without the illustrated gas bubbles retracted to detach a portion of the specimen.

Since the above referenced original provisional application was filed, we have discovered that retraction of pedestal P is less than fully complete. A usual configuration illustrating the collected specimen overlying the specimen is shown in FIG. 1G.

Figure 1H:
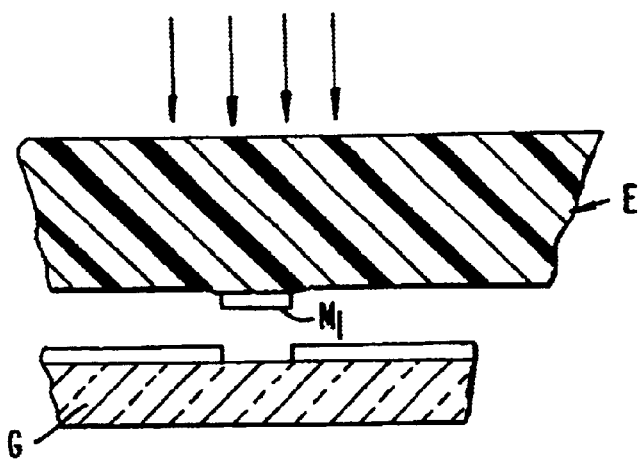
FIG. 1H illustrates the pedestal and specimen of FIG. 1G re-melted with a broad lower power beam to enable the pedestal to substantially return toward the original tape dimension and to retract the micro-dissected specimen further toward the tape to avoid specimen loss and to permit the close gathering of other similar specimens.

Since the filing of the above referenced Provisional Patent Application Serial No. 60/111,662 on Dec. 10, 1998, we have made a discovery. We have discovered that pedestals created during LCM can be attenuated after the microdissection. This attenuation of the pedestal occurs with the use of a second pulse of laser energy. Specifically, after the targeted sample is separated (See FIG. 1G), a second low power and broadly focused beam is targeted at expanded and activated material E. As shown in FIG. 1H, substantially complete retraction of pedestal P occurs. Some discussion of the importance of this discovery is in order.

First, having the selected portion of the specimen M1 protrude from the tape on the end of a pedestal P is not desirable. This sort of protrusion leaves the collected sample vulnerable to being sheared off, or contacting and including other non-specific portions of the specimen. In the first case the desired sample is totally lost. In the second case, nonspecific transfer degrades specimen quality.

Second, and with respect to the expansion and contraction of pedestal P, we find that the use of an expanded pedestal P without gas bubbles produces a predictable and repeatable expansion and contraction of the adhered selected portion of the specimen M1.

Third, the contraction produces little degradation of the selected portion of the specimen M1. Further, we have found the contraction to be substantially complete.

Fourth, the second pulse can be the same power and area of the first pulse. However, we preferred a lower power, longer or more widely dispersed beam as illustrated in FIG. 1H.

We are unsure of the cause of the observed contraction of pedestal P. Surface tension of the activatable material may account for the contraction. Alternately, the activatable material may seek naturally a uniform thickness upon cooling. Alternatively, the retraction caused by the second "annealing pulse" may be due to relaxation of stress induced in the polymer during the capture and/or separation of the target. The retraction only happens when the separation step occurs prior to the second pulse. In any event, we have discovered the observed behavior to be highly useful in non-contact LCM.

Figure 2H:
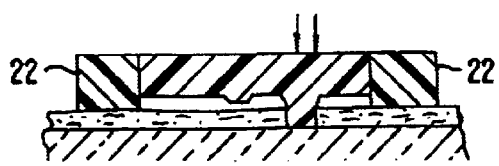

Without the use of the second pulse of radiation to collapse the pedestal P, we have found that the recoil can exceed 50% of the original extension. Thus with our existing EVA polymer used in LCM, we can, for example, activate a 100 micron thick polymer layer to extend 10 microns so as to cross a uniform 5 micron air gap, then impregnate a 5 micron thick tissue slice to which it bonds strongly. On separation from the tissue, the tissue polymer surface retracts ~7 microns (See FIG. 2H) so that this region may be placed again onto a different region of the tissue specimen (which is flat to within 2 microns) without making contact anywhere except the border zone previously mentioned.

Thus repetitive transfer of different spots may be made (by appropriate translation of the film and its substrate) and concentrated (i.e., placed at target-to-target spacing that are much less than those within the tissue section). This may result all desired accumulated elements being concentrated within a small central zone on the transfer surface. Once sufficient homogeneous biological targets have been accumulated on this transfer surface, it may be placed on or in a micro vessel for extraction and molecular analysis.

Figure 4:
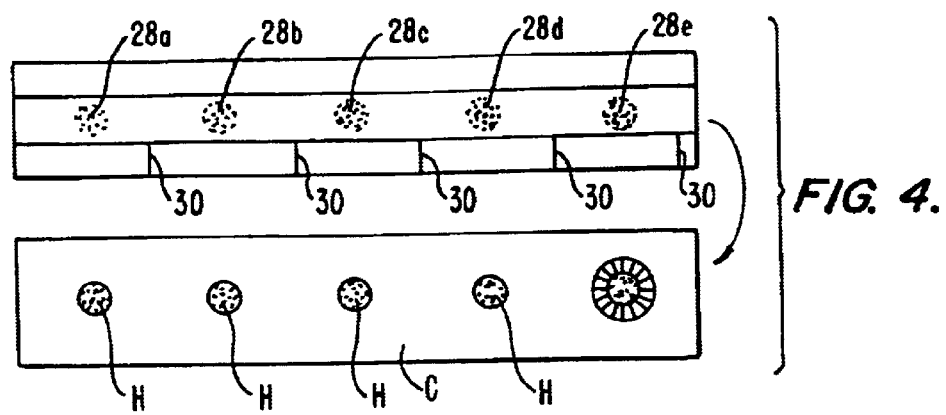
FIG. 4 is an illustrating of a tape similar to the tape produced in FIGS. 3A–3D along side of a sealing array containing a series of encapsulating micro chambers for processing specimen portions collected on the tape of this invention.

A specific refinement of this placement process includes the annular sealing of the thermoplastic film to the open top of a (cylindrical) micro chamber, such as that illustrated in FIG. 4. This can occur in a manner, which seals the chamber with the transferred tissue as biological targets placed at the center of the chamber or the inside surface of the polymer forming the lid.

A further specific refinement uses the thermoplastic sealing properties of the EVA film to form this tight seal either by an annular laser source (or spot scanned in a circle) or by an annular heated pressure plate. This later approach is more easily realized if the substrate on which the recessed thermoplastic polymer was originally formed is relatively thin such as a Mylar (polyester) film less than 200 micron thick.

Referring to FIGS. 2A–2H, a specific preferred geometry is to manufacture a "non stick" polymer tape so that its room temperature thickness is larger than that of the desired thermoplastic adhesive polymer thickness by the amount of the desired recess for the activatible polymer. This can be accomplished by manufacture of the EVA by casting onto the substrate at a higher temperature so that the differential expansion of the EVA and "non stick" border cause the EVA to form a flat surface at the elevated temperature which on cooling leads to the desired recess.

Figure 3A:
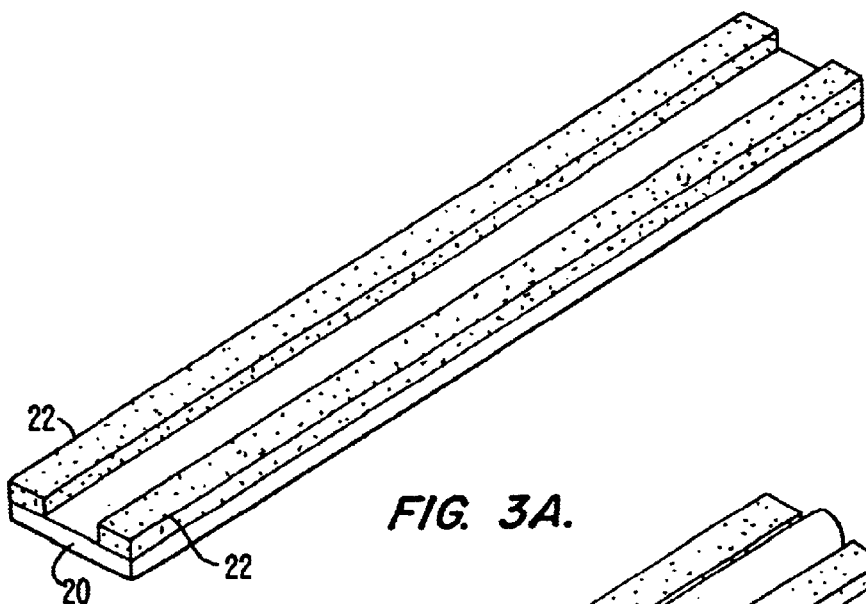
FIG. 3A illustrates a tape like substrate with laminated non sticky borders on either side prior to the placement of an activatable coating between the non sticky borders.
Figure 3B:
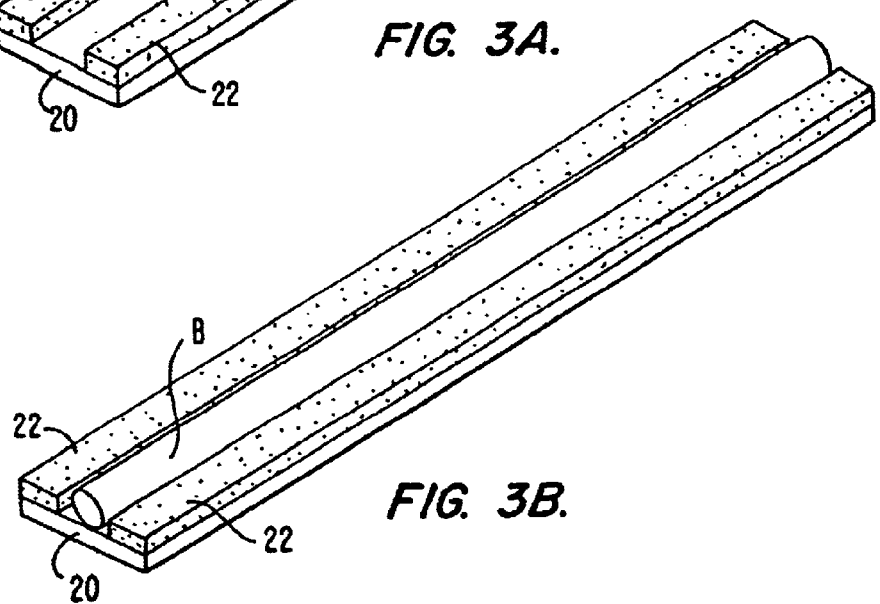
FIG. 3B illustrates a bead of material from which an activatable coating is subsequently formed placed on the substrate of FIG. 3A between the non sticky boarders.
Figure 3C:
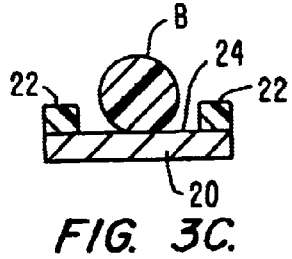
FIG. 3C is a side elevation section of the substrate of FIG. 3B illustrating the bead between the two non-sticky borders.
Figure 3D:
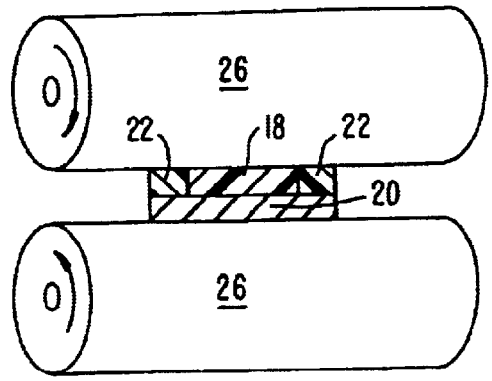
FIG. 3D illustrates schematically hot rolling of the bead of FIG. 3C to form a recessed coating.

Referring to FIG. 2A, substrate 20 has two ridges 22 on either side of a tape like substrate. Substrate 20 is consists of a laminate of 200 micron thick polyester (1 cm wide) with ridges 22 consisting of 200 micron thick strip of polyamide (3 mm wide) on both edges forming central channel 24 which is 4 mm thick. Central channel 24 defines a "U" shaped area (See FIG. 3A) into which fine continuous bead B (rod) of hot ELVAX 410 (with IR absorbing dye) is extruded (See FIGS. 3B and 3C). This then hot rolled by hot rolls 26 by a smooth drum to form a flat surface (See FIG. 2B). As heated, activatible polymer surface 18 is flush with ridges 22 (See FIG. 2B). On cooling the activatable polymer layer contracts on solidification (See FIG. 2C). This leads to a 1-cm wide tape with a 4-mm wide central section of ELVAX 410 on polyester, which is recessed by 20 microns from the border strips of polyamide bonded to the polyester.

Thus we propose a simple scheme for the manufacture of a precision recessed tape for "non contact LCM".

Note that an alternative is to form the same sort of release surface (polyamide) border on a rigid substrate and then fill the central region with EVA.

Referring to FIG. 4, a further refinement of non contact LCM uses a previously disclosed design for periodic marking of the tape so that transfer could be placed periodically in well-defined locations, such as locations 28a–28E. Originally this concept was developed so that the punching out of small-transferred regions into extraction and molecular analysis vessels could be performed without a separate optical location of the transfer regions.

In its present usage, a "non contact LCM" tape can be translated a fixed increment relative to periodic indicator markers 30 on it between each set of LCM transfers (See FIG. 4). As shown in FIG. 4, a set of transfers indicates multiple transfers of individual targets, which are homogeneous, and to be pooled into one sample for molecular analysis. It is possible that much smaller separations between the individual LCM transfers within each set of transfers creates a cluster for each set within a small region (in the example above it might be within 0.5 mm while different sets might be spaced on 2 mm centers).

Referring to the bottom strip of FIG. 4 appearing, it will be seen that capping tape strip C contains spaced micro chambers H. Micro chambers H used for molecular extraction and analysis can be formed as a linear array of wells (with a diameter slightly greater than the individual transfer clusters or d>0.5 mm in the above example) with exactly the same periodic repeat as tape translation between micro transfer sets (2 mm in the example above). This scheme allows a large number of sets of transfers to be accumulated onto the continuous tape and then continuously transferred and (heat) sealed onto the linear array of micro chambers for molecular extraction and analysis. This greatly increases the efficiency of the current LCM process and provides means to reduce the volume of the molecular analysis systems to such small volume that the analysis may be performed more rapidly, at lower reagent cost, and with greater precision. Further this design or its analogues would offer significant advantages for automation of analysis and tracking of samples over the current LCM transfer caps, particularly when incorporating state of the art micro fluidics processing of micro volumes).

Figure 5:
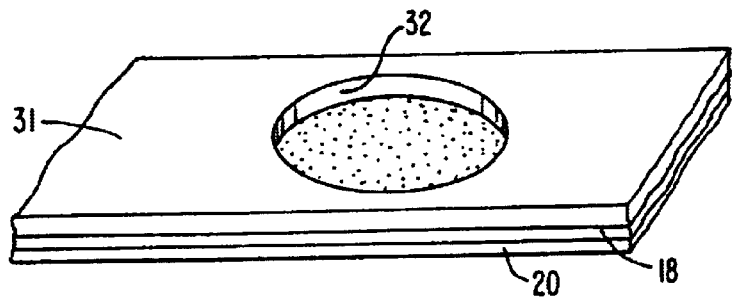
FIG. 5 is a three dimensional picture of a tape having a circular non sticky boundary for practicing the laser capture microdissection of this invention.

Referring to FIG. 5, an alternate embodiment of this invention is illustrated. Specifically, substrate 20 has activatible polymer surface 18 layered completely across the layer. On top of activatible polymer surface 18 is placed coating surface 31 with central periodic aperture 32. This coating and aperture form the desired recess of activatible polymer surface 18 from specimen M.

Figure 6:
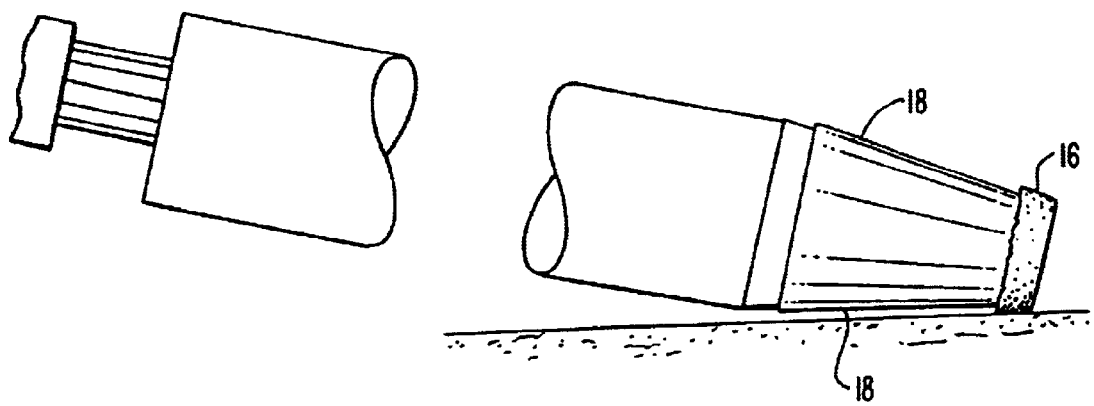
FIG. 6 illustrates a rod like member with a distal rim for spacing the activatable coating on the rod from a specimen where collection of portions of a specimen is occurring.

Referring to FIG. 6 this invention also includes the spacing of activatible polymer surface 18 when the latter surface coats conical end 34 of cylindrical rod R. In order to effect the desired spacing of activatible polymer surface 18 from specimen M, rim 16 is placed—here at the distal end of cylindrical rod R. The reader will understand that since one end of cylindrical rod R is held relative to the specimen, all that is required is that rim 16 contact specimen M. Providing that cylindrical rod R is give an angularity which is aligned to place conical end 34 parallel to specimen M, desired spatial separation from the specimen will occur. For further information regarding this embodiment of surfaces for laser capture microdissection, the reader's attention is invited to U.S. patent application Ser. No. 08/883,821 entitled CONVEX GEOMETRY ADHESIVE FILM SYSTEM FOR LASER CAPTURE MICRODISSECTION by Seth R. Goldstein, et al., one of the named inventors herein.

Figure 7A:
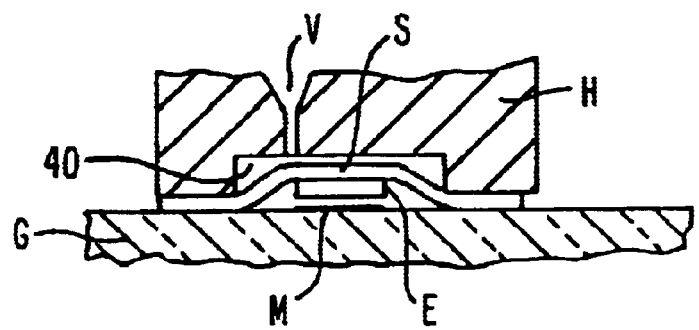
Figure 7B:
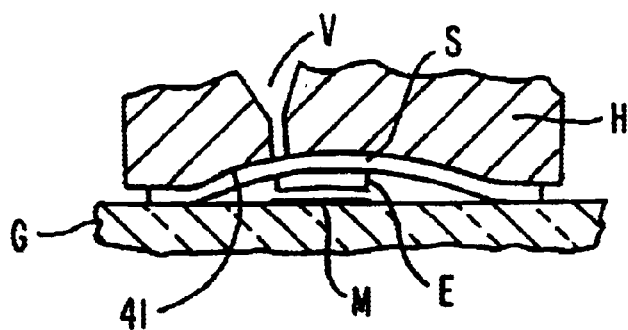
Figure 7C:
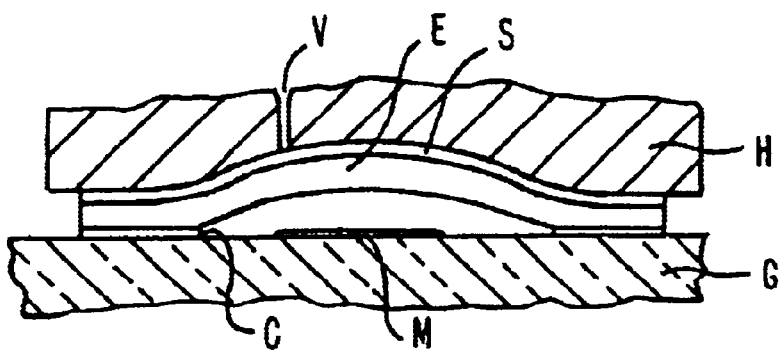

FIGS. 7A–7C all illustrate holders H for the support for substrate S having activatable coatings E. In each case, substrate S is held to holder H by a vacuum applied through a cavity in the holder. In each case, the depth of the cavity is measured to maintain the coating E spaced from the underlying specimen M.

With attention to FIG. 7A, the cavity 40 is rectilinear. Substrate S has sufficient width to extend under holder H and has activatable coating E centrally of the substrate—which is normally in the form of a tape. The depth of cavity 40, substrate S and coating E are such that when vacuum V is applied, activatable coating E is spaced from specimen M on slide G.

FIG. 7B is similar to FIG. 7A with the cavity 41 being rounded. FIG. 7C differs from FIG. 7B in that a very thin coating C which is not sticky to specimen M spaces the substrate S and activatable coating E from the specimen M, activatable coating E in this case extending the full width of substrate S.

Figure 8A:
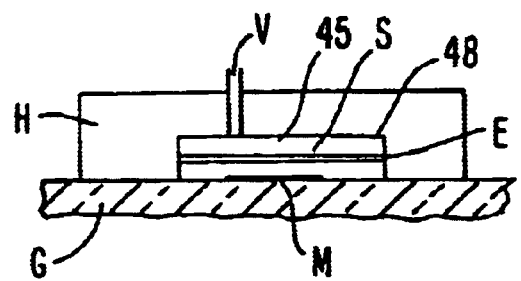
FIGS. 8A and 8B are views embodiments where the tape holder makes contact with the slide or a reference surface relative to the slide where.
Figure 8B:
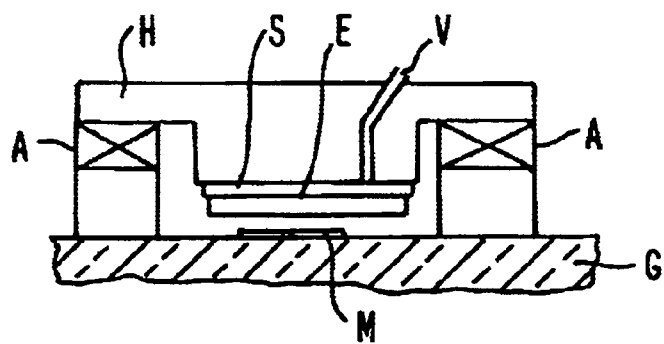

FIGS. 8A and 8B are examples of tape holders H, which are designed to receive and hold a tape strip. As is the case with FIGS. 7A–7C, spacing from specimen M is established by contact with either the slide or the specimen.

Referring to FIG. 8A, holder H is rectilinear with substrate S in the form of tape 45 coated with activatable coating E. Tape 45 is held to holder H by vacuum V with the depth of cavity 48, substrate S, activatable coating E all being designed to preserve the 5 to 20 micron separation.

FIG. 8B differs from FIG. 8A because of actuators A being placed in the sides of holder H. Actuators A are typically precision spacing devices. These allow both precision spacing of activatable coating E from specimen M on slide G as well as assistance in separation of an adhered sample to activatable coating E.

Figure 9:
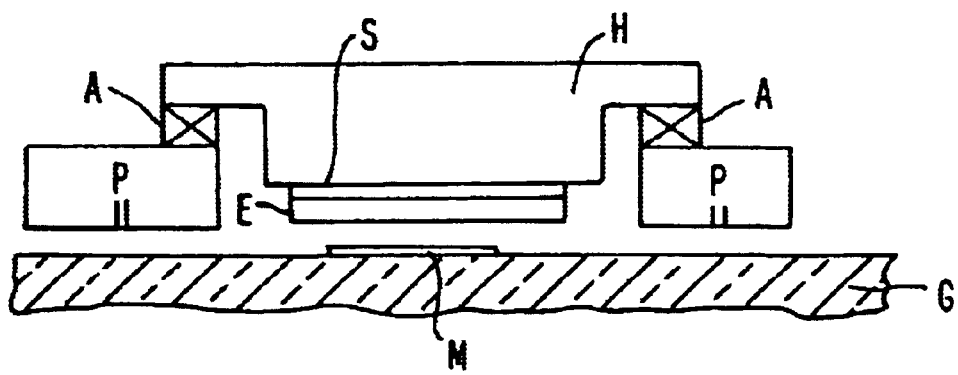
FIG. 9 illustrates an embodiment similar to FIG. 8B where the holder is suspended relative to the slide by an air bearing so that contact between the holder and slide does not occur.

Referring to FIG. 9, air bearings P effect spatial separation of holder H from slide G and specimen M. In all other aspects this embodiment is similar to FIG. 8B.

Figure 10A:
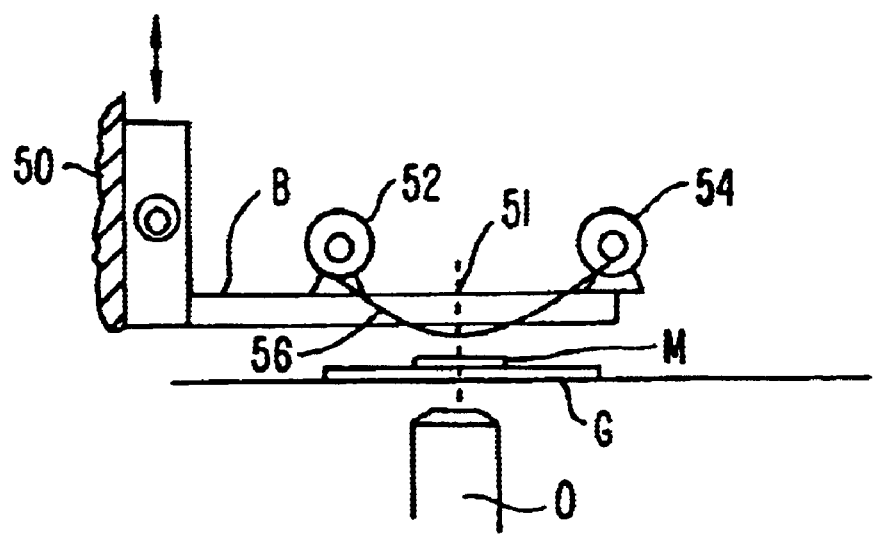
Figure 10B:
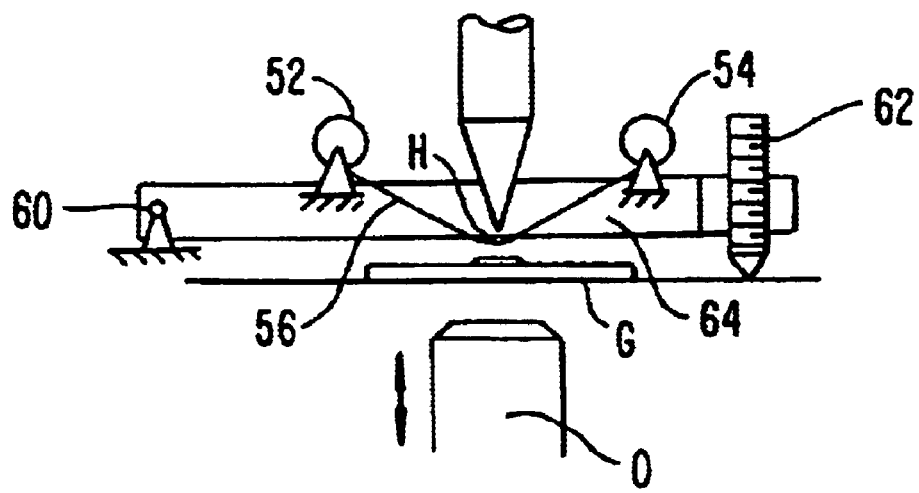
Figure 10C:
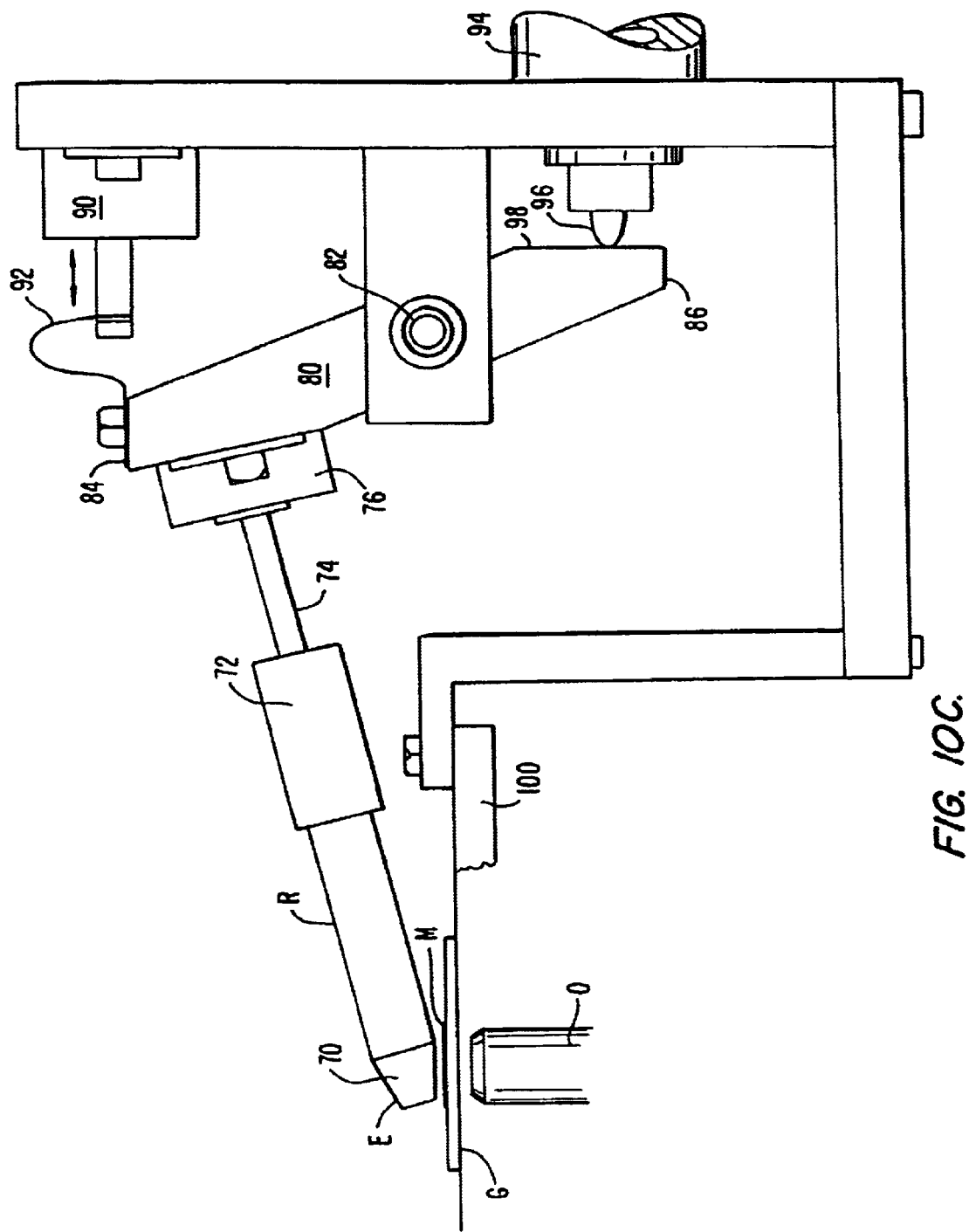

FIGS. 10A–10C all illustrate the case where the activable coating is cantilevered with respect to the sample. The reader will understand that each of these view is utilized with a so-called EPI path—both the view and the activation by laser comes from below specimen M, and locally views and activates the activatable coating from below the specimen.

Referring to FIG. 10A, mechanical slide 50 (schematically shown) supports right angle beam 51. Tape 56 is incrementally fed between reels 52, 54. Slide G having specimen M has microscope objective O below. Adjustment is achieved by having slide 50 move towards and away from slide G and specimen M.

FIG. 10B is similar to FIG. 10A with the exception being the support of reels 52, 54 and tape 56 on simple beam 64. Simple beam 64 has pivot connection 60 and adjustable connection 62. By adjusting adjustable connection 62, towards and away spacing of tape 56 occurs from specimen M on slide G.

Referring to FIG. 10C, a preferred method of cantilever suspension is utilized with the activatable coating being placed on a convex surface at the end of a rod.

Cylindrical rod R has conical surface 70 coated with the activatable coating E. Cylindrical rod R mounts in socket 72 which is in turn concentrically fastened to shaft 74 and stepper motor 76.

Stepper motor 76 is mounted to rocker arm 80 on pivot 82 and is here actuated at upper end 84 and lower ends 86. Specifically course adjustment of the spatial relationship of activatable coating E from specimen M and slide G occurs through lead screw actuator 90 and leaf spring connection to rocker arm 80 at upper end 84. Precision adjustment occurs through differential micrometer 94 at actuator 96 on lower end 86 of rocker arm 80 at actuator surface 98. As can be observed, rocker arm is typically mounted to microscope stage 100.

Operationally, the embodiment of FIG. 10C has proved highly desirable with tolerances of 1 micron being possible between the activatable coating E and specimen M.

Figure 11:
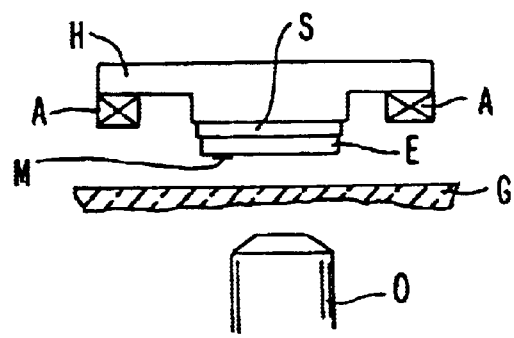
FIG. 11 uses fiducial markings on the lower surface of the tape to effect gauging of the distance between the tissue sample and tape; and, FIG. 12 illustrates actuators and air bearings to establish the required interval between the tissue sample and tape without the requirement risking so-called burs at the severed tape sides.

FIG. 11 illustrates a method of measuring spatial intervals between specimen M and activatable coating E. Referring to FIG. 11, marker M is focused through EPI objective O on the surface of activatable coating E. Such a marker is capable of producing plus or minus about 1 micron.

Figure 12:
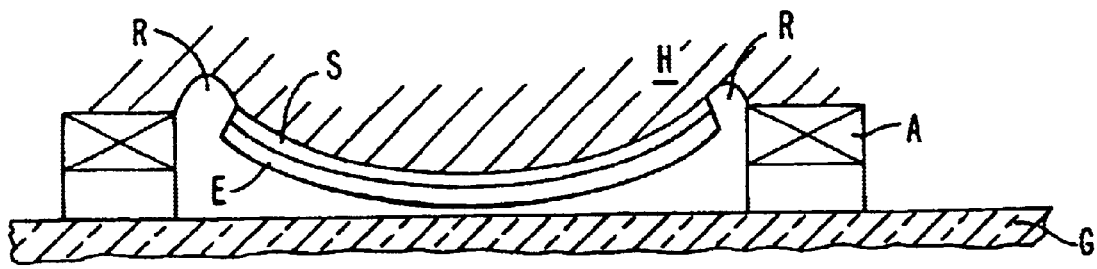

Referring to FIG. 12, it will be seen that substrate S is suspended between two actuators A which are in turn supported on slide G with specimen M there between. It has been found that when many substrates S are coated with activatable coatings E such a EVA, the EVA tends to accumulate in small burrs accumulations along the line of such a cut. The convex cross-section configuration illustrated in FIG. 12 disposes such a burr away from the small gap.

It will be understood that two primary limitations govern the invention set forth herein. First, the activatable coating is always maintained spatially separated from the specimen by a gap. Second, when activated, the activatable coating bridges the gap and at least contacts the specimen M at the targeted area.

It isunderstood that when a flexible tape is used with an "inert substrate" on which a layer of activatable polymer is coated, that the convex surfaces of the substrate and activatable polymer layers can be achieved by conforming the tape to a convex pressure plate.

Every material generally has a quasi linear expansion coefficient over some narrow range of temperatures. The noncontact capture requires that focal expansion is much greater that the expansion of the surrounding layer. Although we heat the polymer focally during and after the end of the pulse the heat continues to flow radially causing the surrounding material to expand in proportional to the heating assuming linear thermal expansion. In fact, the larger volume changes on phase change associated with an activated polymer [i.e., melting or melting and vaporization/expansion of an included air bubble] greatly facilitate noncontact LCM compared to a simple linear thermal expansion and allow big expansions to be highly localized.

Note the heating can be concentrated locally by the laser beam size and short pulse length—however heat will flow radially after the end of the pulse and is therefore not completely confined to the local activation region. However we can confine the volume to which sufficient heating occurs to melt the polymer. In our usage of Noncontact LCM, this phase change (or a smaller vapor bubble created within it) is associated with a large volume expansion compared to the much smaller linear expansion coefficient of the surrounding solid "unactivated" polymer and its "inert" substrate. Since the surrounding "unmelted" structures are "rigid", the expanded melted volume is forced to flow across the "gap" to contact and capture the desired target in the specimen.

It is not required that the activatable coating E become sticky to the visualized area of specimen M upon activation. For example, the activatable coating could be provided with a surface that is always sticky with respect to specimen M. Further, such a coating can have selective attachment to the specimen. For example, the coating may attach preferentially to certain proteins in the activated areas.

What is claimed is:

1. A process of laser capture microdissection of at least a portion from a specimen having the steps of:

providing a selectively activatable layer which upon activation becomes adhesive to a portion of the specimen and volumetrically expands with the volumetric expansion exceeding a first interval taken normal to a surface of the selectively activatable layer;

placing the selectively activatable layer overlying the specimen at a finite separation less than the first interval without contacting the specimen;

selectively activating the selectively activatable layer to cause volumetric expansion at least to the first interval to locally contact a portion of the specimen at the extremity of the volumetric expansion and become adhesive to the portion of the specimen; and, separating the selectively activatable layer from the specimen to microdissect the contacted portion of the specimen from the remainder of the specimen after selective activation.

2. The process of laser capture microdissection from a specimen according to claim 1 having the steps of:

providing a supporting substrate; and, adhering the selectively activatable layer to the supporting substrate.

3. The process of laser capture microdissection from a specimen according to claim 1 having the steps of:

before the selectively activating step, visualizing the portion of the specimen to locate the portion of the specimen for microdissection; and, activating the selectively activatable layer overlying the visualized portion of the specimen.

4. The process of laser capture microdissection from a specimen according to claim 1 where the selectively activating step forms a mechanical bond with the specimen.

5. The process of laser capture microdissection from a specimen according to claim 1 wherein:

a selectively activatable layer is provided with a coating on one side of the selectively activatable layer, the coating having an affinity specific bond with the specimen, wherein upon activation, the coated selectively activatable layer can be contacted to the specimen to form affinity specific bonds with the portion of the specimen.

6. The process of laser capture microdissection from a specimen according to claim 1 having the steps of:

repeating the placing, selectively activating, and separating steps at different portions of the specimen with different parts of the selectively activatable layer to capture a series of portions of the specimen on the selectively activatable layer.

7. The process of laser capture microdissection from a specimen according to claim 6 having the steps of:

moving the selectively activatable layer with respect to the specimen to microdissect and concentrate the series of portions of the specimen on the selectively activatable layer.

8. A process of attachment of a selectively activatable layer to a portion of a specimen having the steps of:

providing a selectively activatable layer which upon laser activation causes heat generated volumetric expansion of an extremity to a first interval taken normal to the surface of the selectively activatable layer and upon cooling elastically contracts the extremity towards the activatable layer, the extremity of the volumetric expansion becoming adhesive with respect to the specimen during and after activation;

placing the selectively activatable layer overlying the specimen at a portion for microdissection at a separation less than the first interval without contacting the specimen; and, selectively activating with laser energy to heat the selectively activatable layer to cause heat generated volumetric expansion of the extremity to a first interval taken normal to the surface of the selectively activatable layer to contact the portion of the specimen and adhere to the portion of the specimen;

ceasing the laser activation; and, allowing the heated selectively activatable layer to cool and elastically contract the extremity towards the activatable layer while maintaining adherence to the portion of the specimen.

9. The process of attachment of a selectively activatable layer to a portion of a specimen according to claim 8 wherein:

the heated selectively activatable layer is allowed to cool and elastically contract the extremity towards the activatable layer while maintaining adherence to the portion of the specimen to microdissect and pull away the portion of the specimen from a remainder of the specimen.

10. The process of attachment of a selectively activatable layer to a portion of a specimen according to claim 8 wherein:

the volumetric expansion is contracted by cooling while maintaining attachment to the portion of the specimen to elastically tension the volumetric expansion of the activatable layer; and, withdrawing the activatable layer from the specimen to separate and thus microdissect the portion of the specimen from the remainder of the specimen.

11. The process of attachment of a selectively activatable layer to a portion of a specimen according to claim 8 wherein:

the volumetric expansion is contracted at the extremity to withdraw the portion of the specimen bonded to the volumetric expansion within the first interval whereby the portion of the specimen bonded to the extremity of the volumetric expansion cannot contact underlying and remaining portions of the specimen.

12. The process of attachment of a selectively activatable layer to a portion of a specimen according to claim 8 wherein:

the activatable layer is provided with a volume chance associated with phase transistion.

13. The process of attachment of a selectively activatable layer to a portion of a specimen according to claim 8 wherein:

the activatable layer is attached to a supporting substrate.

14. A process of laser capture microdissection from a specimen having the steps of:

providing a selectively activatable layer which upon activation by laser causes volumetric expansion upon heating beyond a first interval and becomes adhesive to a specimen;

placing the selectively activatable layer overlying the specimen at a separation less than a first interval without contacting the specimen;

heating and expanding the selectively activatable layer to cause volumetric expansion first by locally heating and expanding a first inner volume of the selectively activatable layer with a component of expansion normal to the selectively activatable layer to cause an extremity of expansion away from the activatable layer;

heating and expanding a second volume of the selectively activatable layer surrounding the first volume with a component of expansion in a plane of the selectively activatable layer into the first volume whereby a total volumetric expansion occurs with the second volume expanding into and extruding the first volume at the extremity for a total expansion at least to the first interval to locally contact a portion of the specimen with the extremity of the volumetric expansion and adhere to the portion of the specimen; and, removing the extremity of the volumetric expansion with the portion of the specimen attached to microdissect the portion from the sample.

15. The process of laser capture microdissection from a specimen according to claim 14 having the steps of:

generating a vapor bubble in the first volume during heating and expanding of the first volume whereby the vapor bubble contributes to the volumetric expansion of the first volume.

\* \* \* \* \*